(12) United States Patent
Leddy et al.

(10) Patent No.: US 7,691,638 B2
(45) Date of Patent: Apr. 6, 2010

(54) METHODS FOR DETERMINING ELECTRON TRANSFER RATES IN METALLOPROTEINS

(75) Inventors: Johna Leddy, Iowa City, IA (US); Shelley D. Minteer, Pacific, MO (US)

(73) Assignee: University of Iowa Research Foundation, Iowa City, IA (US)

( * ) Notice: Subject to any disclaimer, the term of this patent is extended or adjusted under 35 U.S.C. 154(b) by 804 days.

(21) Appl. No.: 10/406,000

(22) Filed: Apr. 3, 2003

(65) Prior Publication Data

US 2004/0053416 A1   Mar. 18, 2004

Related U.S. Application Data

(60) Provisional application No. 60/369,344, filed on Apr. 3, 2002.

(51) Int. Cl.
*G01N 33/20* (2006.01)
(52) U.S. Cl. .............................. 436/76; 435/25; 436/81; 436/83; 436/84; 436/86; 436/183; 702/19; 702/22; 702/27; 702/30; 703/2; 703/11
(58) Field of Classification Search ................ 435/25; 436/73, 76, 81, 83–84, 86, 94, 96, 106, 183; 700/268; 702/19, 22, 27, 30; 703/2, 11–12
See application file for complete search history.

(56) References Cited

OTHER PUBLICATIONS

Meisel, D. et al, Journal of the American Chemical Society 1976, 98, 7505-7510.*
Chou, M. et al, Journal of the American Chemical Society 1977, 99, 5615-5623.*
Finkenberg, E. et al, Journal of Physical Chemistry 1978, 82, 526-531.*
Ohno, T. et al, Journal of Physical Chemistry 1984, 88, 1670-1674.*
Hupp, J. T. et al, Journal of Physical Chemistry 1985, 89, 2795-2804.*
Nadler, W. et al, Journal of Chemical Physics 1987, 86, 3906-3924.*
Onuchic, J. N. et al, Journal of Chemical Physics 1990, 92, 722-733.*
Schulten, K. et al, Chemical Physics 1991, 158, 421-446.*
Chuev, G. N. et al, Journal of Theoretical Biology 1993, 163, 51-60.*
Rasaiah, J. C. et al, Journal of Chemical Physics 1993, 98, 1213-1227.*
Siddarth, P. et al, Journal of Physical Chemistry 1993, 97, 2400-2405.*
Andrew, S. M. et al, Journal of the American Chemical Society 1993, 115, 5516-5521.*
Drago, R. S. et al, Journal of Physical Chemistry 1995, 99, 6563-6569.*
Zhou, H.-X. et al, Journal of Chemical Physics 1995, 103, 3481-3494.*

(Continued)

*Primary Examiner*—Arlen Soderquist
(74) *Attorney, Agent, or Firm*—J. Steven Rutt; Foley & Lardner LLP (57) ABSTRACT

The present invention is directed to methods for determining electron transfer rates in systems involving metalloproteins. Metalloprotein/substrate electron transfer rates as well as metalloprotein self exchange rates may be modeled. Such electron transfer rates are useful in smart drug design and enzyme engineering.

13 Claims, 4 Drawing Sheets

OTHER PUBLICATIONS

Ichiye, T., Journal of Chemical Physics 1996, 104, 7561-7571.*
Aich, S. et al, Journal of Physical Chemistry A 1998, 102, 722-729.*
Burshtein, A. I. et al, Journal of Physical Chemistry A 1998, 102, 816-824.*
Sharp, K. A., Biophysical Journal 1998, 74, 1241-1250.*
Miyashita, O. et al, Journal of Physical Chemistry B 1999, 103, 562-571.*
Bominaar, E. L. et al, Journal of Chemical Physics 1999, 110, 11411-11422.*
Rosso, K. M. et al, Journal of Physical Chemistry A 2000, 104, 6718-6725.*
Formosinho, S. J. et al, Research on Chemical Intermediates 2001, 27, 103-124.*
Burnshtein, A. I. et al, Physical Chemistry Chemical Physics 2001, 3, 198-203.*
Solc, M., Berichte der Bunsen-Gesellschaft 1970, 74, 1244-1248.*
Ablett, S. et al, Journal of Solution Chemistry 1975, 4, 797-807.*
Doba, T. et al, Memoirs of the Faculty of Engineering, Hokkaido University 1976, 14, 55-63.*
Schulten, Z. et al, Journal of Chemical Physics 1977, 66, 4616-4634.*
Endicott, J. F. et al, Journal of the American Chemical Society 1983, 105, 5301-5310.*
Macartney, D. H. et al, Inorganic Chemistry 1983, 22, 3530-3534.*
Belorizky, E. et al, Chemical Physics Letters 1988, 145, 33-38.*
Larsson, S., Chemica Scripta 1988, 28A, 15-20.*
Herbert, R. G. et al, Journal of Molecular Liquids 1989, 41, 207-222.*
Bosco, E., Journal of Electroanalytical Chemistry 1994, 379, 509-511.*
Occhialini, D. et al, Journal of Electroanalytical Chemistry 1994, 369, 39-52.*
Northrup, S. H., Protein Electron Transfer 1996, 69-97, Editor: Bendall, Derek S., Publisher: Minerals, Metals & Materials Society, Warrendale, Pa.*
Pohlmann, L. et al, Berichte der Bunsen-Gesellschaft 1996, 100, 2097-2102.*
Cho, K. C. et al, Journal of the American Chemical Society 1986, 108, 2814-2818.*
Cho, K. C. et al, Journal of Physical Chemistry 1987, 91, 3690-3693.*
Coury, Jr., L. A. et al, Journal of Physical Chemistry 1991, 6034-6040.*
Sumi, H., Journal of Physical Chemistry 1996, 4831-4839.*
A.G. Mauk et al., "Distances of Electron Transfer to and from Metalloprotein Redox Sites in Reactions with Inorganic Complexes," J. Amer. Chem. Soc., vol. 102(13), Jun. 18, 1980, pp. 4360-4363.
H.L. Hodges et al., "Kinetic Studies of the Reduction of Ferricytochrome $c$ by Fe(EDTA)$^{2-}$," J. Amer. Chem. Soc., vol. 96(10), May 15, 1974, pp. 3132-3137.
D. Cummins et al., Electron-Transfer Protein Reactivities. Kinetic Studies of the Oxidation of Horse Heart Cytochrom $c$, *Chromatium vinosum* High Potential Iron-Sulfur Protein, *Pseudomonas aeruginosa* Asurin, Bean Plastocyanin, and *Rhus vernicifera* Stellacyanin by Pentaamminepyridineruthenium(III), J. Amer. Chem. Soc., vol. 99(15), Jul. 20, 1977, pp. 5158-5167.
A.G. Mauk et al., "Analysis of the Kinetics of Electron Transfer between Blue Copper Proteins and Inorganic Redox Agents. Reactions Involving Bis(dipicolinate) Complexes of Cobalt(III) and Iron(II) and Stellacyanin, Plastocyanin, and Azurin," J. Amer. Chem. Soc., vol. 104, 1982, pp. 7654-7657.
J. Rawlings et al., "Kinetic Studies of the Oxidation and Reduction of *Chromatium* High Potential Iron-Sulfur Protein (HiPIP) by Inorganic Complexes. Comparison of the Electron Transfer Reactivities of HiPIP and Horse Heart Cytochrome $c$," J. Amer. Chem. Soc., vol. 98(8), Apr. 14, 1976, pp. 2177-2180.
R.A. Holwerda et al., "Comparison of the Electron-Transfer Reactivities of Tris(oxalato)cobaltate(III) (Co(ox)$_3^{3-}$) and Tris(1,10-phenanthroline)cobalt(III) (Co(phen)$_3^{3+}$) with Metalloproteins," J. Amer. Chem. Soc., vol. 102(3), Jan. 30, 1980, pp. 1142-1146.
A.G. Mauk et al., Bis(dipicolinate) Complexes of Cobalt(III) and Iron(II) as New Probes of Metalloprotein Electron-Transfer Reactivity. Analysis of Reactions Involving Cytochrome $c$ and Cytochrome $c_{551}$, J. Amer. Chem. Soc., vol. 101(17), Aug. 15, 1979, pp. 5054-5056.
S. Wherland et al., "Electron Transfer Mechanisms Employed by Metalloproteins," Biological Aspects of Inorganic Chemistry, 1977, pp. 289-368.

* cited by examiner

| Protein | Experimental | Marcus Theory | Spin Diffusion/Marcus Theory |
|---------|--------------|---------------|------------------------------|
| Cytochrome c | $5.0 \times 10^4$ | $5 \times 10^1 - 4 \times 10^8$ | $5.21 \times 10^4$ |
| Stellacyanin | $1.2 \times 10^5$ | $5 \times 10^5 - 7 \times 10^7$ | $9.51 \times 10^4$ |
| HIPIP | $2.2 \times 10^4$ | $2 \times 10^{-2} - 8 \times 10^4$ | $1.96 \times 10^4$ |
| Plastocyanin | $2.0 \times 10^4$ | $2 \times 10^{-1} - 2 \times 10^6$ | $4.33 \times 10^4$ |

Figure 1

|  | Cytochrome c | Stellacyanin | HIPIP | Plastocyanin |
|---|---|---|---|---|
| R (Å) | 16.6 | 19.5 | 15.5 | 15.8 |
| $E^0$(mV) | 260 | 184 | 350 | 350 |
| g | 6 | 2.18 | 2.08 | 2.14 |
| A (G) | 98 | 138 | 176 | 197 |
| $R_{pr}$(Å) | 2.3 | 2.0 | 3.5 | 2.4 |
| $Z_{initial}$ | 7.5 | 0 | −2.5 | −9 |
| $Z_{final}$ | 6.5 | 0 | −3.5 | −10 |

Figure 2

| Substrate | $k_{11}$ (M$^{-1}$s$^{-1}$) | $\delta$ (Å) | g |
|---|---|---|---|
| Ru(NH$_3$)$_5$py$^{+3}$ | $4.7 \times 10^5$ | 8.40 | 2.7 |
| Co(phen)$_3^{-3}$ | 42 | 13.6 | 4.0 |
| Fe(EDTA)$^{-2}$ | $3.0 \times 10^4$ | 8.00 | 2.0 |
| Co(ox)$_3^{-3}$ | $2.8 \times 10^{-7}$ | 9.00 | 4.0 |

Figure 3

| Substrate | Cytochrome c | Plastocyanin | HIPIP | Stellacyanin |
|---|---|---|---|---|
| Ru(NH$_3$)$_5$py$^{+3}$ | $9.26 \times 10^3$ | $7.10 \times 10^3$ | $1.10 \times 10^3$ | $1.94 \times 10^5$ |
| Co(phen)$_3^{+3}$ | $1.50 \times 10^3$ | $4.90 \times 10^3$ | $2.80 \times 10^3$ | $1.80 \times 10^5$ |
| Fe(EDTA)$^{-2}$ | $2.57 \times 10^4$ | $8.20 \times 10^4$ | $1.70 \times 10^3$ | $4.30 \times 10^5$ |
| Co(ox)$_3^{-3}$ |  | $2.40 \times 10^{-1}$ |  |  |

Figure 4

| Substrate | Cytochrome c | Plastocyanin | HIPIP | Stellacyanin |
|---|---|---|---|---|
| $Ru(NH_3)_5py^{+3}$ | 4.7 | 4.8 | 5.9 | 4.4 |
| $Co(phen)_3^{+3}$ | 8.6 | 7.9 | 7.8 | 6.8 |
| $Fe(EDTA)^{-2}$ | 7.5 | 6.9 | 9.9 | 4.1 |
| $Co(ox)_3^{-3}$ |  | 8.6 |  |  |

Figure 5

| Substrate | Cytochrome c | Plastocyanin | HIPIP | Stellacyanin |
|---|---|---|---|---|
| $Ru(NH_3)_5py^{+3}$ | 2.3 | 2.4 | 3.5 | 2 |
| $Co(phen)_3^{+3}$ | 3.6 | 2.9 | 2.8 | 1.8 |
| $Fe(EDTA)^{-2}$ | 5.3 | 4.7 | 7.7 | 1.9 |
| $Co(ox)_3^{-3}$ |  | 5.9 |  |  |

Figure 6

| Substrate | Cytochrome c | Plastocyanin | HIPIP | Stellacyanin |
|---|---|---|---|---|
| $Ru(NH_3)_5py^{+3}$ | $1.89 \times 10^4$ | $1.74 \times 10^3$ | $4.88 \times 10^3$ | $2.45 \times 10^5$ |
| $Co(phen)_3^{+3}$ | $7.72 \times 10^3$ | $1.19 \times 10^4$ | $5.79 \times 10^3$ | $2.11 \times 10^5$ |
| $Fe(EDTA)^{-2}$ | $3.26 \times 10^3$ | $4.43 \times 10^3$ | $1.01 \times 10^3$ | $2.68 \times 10^5$ |
| $Co(ox)_3^{-3}$ |  | $2.33 \times 10^{-1}$ |  |  |

METHODS FOR DETERMINING ELECTRON TRANSFER RATES IN METALLOPROTEINS

This application claims the benefit of U.S. Provisional Application No. 60/369,344, filed on Apr. 3, 2002.

BACKGROUND OF THE INVENTION

1. Field of the Invention

The present invention is directed to methods for determining electron transfer rates in systems containing metalloproteins. Such methods may be used, for example, to model the electron transfer rate between a metalloprotein and a substrate or the self-exchange rate of a metalloprotein and based on the model to design drugs and engineer proteins tailored to enhance or diminish the efficiency of catalytic processes.

2. Background of the Related Art

Propagation of the spin of an unpaired electron through space is referred to as spin diffusion. Spin diffusion can be treated similarly to physical diffusion of molecules. As a spin diffuses through space, the induced magnetization is transferred through space. Magnetization is analogous to concentration, and changes in space as a function of time. Like mass transfer, magnetization transfer through a molecule is characterized by a spin diffusion coefficient (D). Like Fick's Law for mass transfer, magnetization transfer is defined by the modified Bloch equations [48]. The Bloch equation for magnetization transfer through both the process of relaxation and spin diffusion is shown in Equation 1.

$$\frac{\partial M}{\partial t} = \frac{g\beta M \cdot H}{\hbar} + D\nabla^2 M \quad (1)$$

where M is the magnetization, H is magnetic field, $\beta$ is the Bohr magneton, and g is the electronic g factor. The spin diffusion coefficient is equal to $Wa^2$, where W is the spin flip-flop probability pet second ($\sim 10^3 \text{sec}^{-1}$) and a is the nearest neighbor distance. The actual value of the spin flip-flop probability per second is equal to one fiftieth of the inverse of the spin-spin relaxation time, $$W = \frac{1}{50T}.$$

Paramagnetic metal centers of proteins can induce large magnetic fields. However, the decay length of the field is less than the distance between the metal center and the surface active site. Thus, the field at the substrate is well approximated as that of the earth's magnetic field. Because protein/substrate electron transfer reactions occur within the earth's magnetic field, the spin relaxation portion of the Bloch equation ($g\beta M \cdot H/\hbar$) is negligible. The Bloch equation then simplifies to Equation 2, which is directly analogous to Fick's second law. The spin diffusion coefficient is a function of the overall conjugation of the protein and the existing electron withdrawing groups.

$$\frac{\partial M}{\partial t} = D\nabla^2 M \quad (2)$$

If the electron transfer between protein and substrate occurs though a spin polarization pathway, the spin must diffuse from the metal center to the surface active site before spin polarization can occur. Therefore, the electron transfer will occur in two steps; the first step is spin diffusion to the surface active site and the second step is the spin polarization/electron transfer. The overall electron transfer rate will be a function of these two steps.

One third of all proteins are metalloproteins. Metalloproteins include a metal center, such as Fe, Ca, Cu or Zn, and a protein structure, typically composed of elements such as carbon, nitrogen, oxygen, hydrogen and sulfur, surrounding the metal center. For instance, hemoglobin, which carries oxygen in the bloodstream, is an iron containing metalloprotein.

Two areas where electron transfer reactions may be important are smart drug design and enzyme engineering.

In enzyme engineering, the structure of an enzyme is altered to change its catalytic rates and processes. This may be done, for instance, to increase rates and thus product generation. Similarly, an enzyme could be engineered to avoid making unwanted side products.

In drug design, drugs are designed that act as a substrate and alter the rate of an enzymatic reaction, either faster or slower. The substrate might, for instance, block the active site.

Prior art methods for determining the electron transfer rates of metalloproteins have been shown to be inaccurate. For instance, electron transfer rates determined according to conventional Marcus Theory typically differ from experimentally observed values by four to seven orders of magnitude.

Therefore, there exists a need in the art for a method by which to model electron transfer rates in metalloprotein systems more accurately. Examples include metalloprotein/substrate electron transfer rates and metalloprotein self exchange rates.

SUMMARY OF THE INVENTION

An object of the invention is to solve at least the above problems and/or disadvantages and to provide at least the advantages described hereinafter.

Accordingly, a first embodiment of the present invention is directed to a method for determining the electron transfer rate between a metalloprotein and a substrate, which comprises modeling a metalloprotein to determine the distance from a metal center of the metalloprotein to a surface active site of the metalloprotein; determining the spin diffusion rate, which corresponds to the rate that the spin diffuses from the metal center to the surface active site; determining an intermediate electron transfer rate value, using the self exchange rate of the metalloprotein, the self exchange rate of a substrate, the stability constant of the metalloprotein/substrate complex, and the collision frequency of the metalloprotein and substrate; and modifying the intermediate electron transfer rate value using the spin diffusion rate to yield the electron transfer rate between the metalloprotein and the substrate.

A second embodiment of the present invention is directed to a method for determining the overall self-exchange rate for a metalloprotein, which comprises: modeling a metalloprotein to determine the distance from a metal center of the metalloprotein to a surface active site of the metalloprotein; determining the spin diffusion rate, which corresponds to the rate that the spin diffuses from the metal center to the surface active site; determining the low magnetic field steady state approximation or Marcus theory based approximation of self-exchange rates of the surface active site of the metalloprotein; and coupling the spin diffusion rate and the low magnetic field steady state approximation of the surface active site to yield the self-exchange rate for the metalloprotein.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

According to the present invention, protein/substrate electron transfer reactions and protein self-exchange reactions were modeled for a variety of well-defined systems, according to the two step model, i.e., spin diffusion to the surface active site followed by spin polarization/electron transfer. The model yields the protein/substrate electron transfer reaction rates and protein self-exchange reaction rates within an order of magnitude of experimentally derived values.

The complexity of biological systems makes it very difficult to model electron transfer reaction in proteins with any precision. Strict Marcus theory models for electron transfer in proteins can only predict electron transfer rates to within a range of from about 2 to 7 orders of magnitude of experimentally derived values. See, Mauk, et al., *J. Am. Chem. Soc.*, 102, 4360-4363 (1980); Hodges, et al, *J. Am. Chem. Soc.*, 96, 3132-3137 (1974); Cummings, et al., *J. Am. Chem. Soc.*, 99, 5158-5167 (1977); Mauk, et al., *J. Am. Chem. Soc.*, 104, 7654-7657 (1982); Rawlings, et al., *J. Am. Chem. Soc.*, 98, 2177-2180 (1976); Holwerda, et al. *J. Am. Chem. Soc.*, 102, 1142-1146 (1980); Wherland, et al, "Electron Transfer Mechanism Employed by Metalloproteins" in *Biological Aspects of Inorganic Chemistry*, Wiley, New York, 1977, pp. 289-368; and Mauk, et al., *J. Am. Chem. Soc.*, 101, 5054-5056 (1979).

From Marcus theory, the spin polarization-based electron transfer rates are determined for each substrate/protein complex in the presence of the earth's magnetic field. Relative Marcus theory has been widely used to model outer-sphere electron transfer reactions of proteins and substrates. This theory relates the electron transfer rate ($k_{12}$) to the self-exchanges rates of the two reactants ($k_{11}$ and $k_{22}$), the overall equilibrium constant or stability constant to form the reactant complex between the protein and substrate ($K_{12}$), and the collision frequency for the reactants in solution (Z). This relationship is shown in Equation 3.

$$k_{12} = \sqrt{k_{11}k_{22}K_{12}\exp\left(\frac{(\ln K_{12})^2}{4\ln(k_{11}k_{22}Z^{-2})}\right)} \quad (3)$$

Traditionally, this model has been used to predict protein self-exchange rates from measured protein/substrate electron transfer rates. For a single protein and several different substrates, the protein self-exchange rates predicted by Equation 3 will typically vary over 4 to 7 orders of magnitude. Because the self-exchange rates for the protein are independent of the substrate, the model has no predictive power for metalloproteins.

The present invention couples Marcus theory with spin diffusion/spin polarization-based calculations of self-exchange rates to determine protein/substrate electron transfer rates for the protein. These self-exchange calculations were performed using steady state approximations including spin diffusion. In metalloproteins, the spin must first diffuse from the metal center to the surface active site of the protein. This spin diffusion has a rate $k_{SD}$. The spin diffusion rate is calculated using Equation. 4.

$$k_{SD} = \frac{D}{R^2} \quad (4)$$

where D is the spin diffusion coefficient (approximately $10^{-11}$ cm$^2$/s for proteins) and R is the distance from the metal center through the molecular framework to the surface active site. The low magnetic field steady state approximation of self-exchange rates of the surface active sites is shown in equation 5.

$$k_{NN}(H) \cong \frac{g\beta M}{\hbar \pi} + \frac{A\beta}{2\hbar} \quad (5)$$

where the magnetic field (H) is approximately 1 Gauss. The overall self-exchange rate of the protein is calculated as the sum of the time it takes for both the spin diffusion and spin polarization-based electron transfer to occur. The overall self-exchange rate ($k_{NN}$) for a protein/protein complex is shown in Equation 6.

$$k_{NN} = \frac{k_{SD}k_{NN}(H)}{k_{SD} + k_{NN}(H)} \quad (6)$$

The bimolecular rate for the overall self-exchange mechanism is determined by the product of the self-exchange rate ($k_{NN}$) and the stability constant (K) for forming the protein/protein complex, as seen in Equation 64.

$$k_{ex} = K k_{NN} \quad (7)$$

The stability constant (K) describes the formation of the complex of the two reactants (protein/protein or protein/substrate) which precedes the spin diffusion and spin polarized electron transfer step. The stability constant is calculated from the following equation:

$$K = \frac{4\pi N r^3}{3000} \exp\left(-\frac{z_1 z_2 e^2}{\epsilon r RT}\right) \quad (8)$$

where N is Avogadro's number, r is the distance of closest approach of the two reactants, $z_1$ and $z_2$ are the charges of the two reactants, $\epsilon$ is the charge on an electron, and $\epsilon$ is the dielectric constant of the medium. $\epsilon$ is 78 in water. The stability constant does not depend on the magnetic field. All self-exchange rates reported are bimolecular rates ($k_{ex}$)

The magnetically enhanced bimolecular electron transfer rate ($k_{12}$) is determined by substituting the spin diffusion dependent value for the self exchange rates of the protein ($k_{ex}$) and the self-exchange rate of the substrate ($k_{22}$) from Equation 5 into Equation 3. This electron transfer rate is for the electron transfer between the surface active site of the protein and the redox couple center (substrate). The spin must first diffuse from metal center to the surface active site, with a rate $k_{SD}$ from Equation 4. Because the overall reaction occurs in two steps (spin diffusion and electron transfer), the overall bimolecular electron transfer rate is set by the preequilibrium complex formation ($K_{12}$) and the sum of the time for spin diffusion and electron transfer, given as Equation 9.

$$k = \frac{K_{12} k_{SD} \frac{k_{12}}{K_{12}}}{k_{SD} + \frac{k_{12}}{K_{12}}} = \frac{k_{SD} k_{12}}{k_{SD} + \frac{k_{12}}{K_{12}}} \quad (9)$$

The overall reaction rate from Equation 9 was used to calculate each protein/substrate electron transfer rate.

The methods according to embodiments of the present invention were used to model electron transfer rates for the following metalloproteins: horse heart cytochrome c, stellacyanin (*Rhus vernificfera*), plastocyanin (*Phaseolus vulgaris*), and HIPIP (*Chromatium vinosurn*). Stellacyanin and plastocyanin are blue copper proteins. Both proteins are EPR active with electronic g factors between 2.14-2.18. Horse heart cytochrome c has an iron metal center with a high spin electronic g factor of 6. NIPIP also has an iron metal center, but it is low spin with a electronic g factor of 2.08. These proteins have a wide variety of well-characterized physical and chemical properties, including size, metal center, charge, distance to surface active site, and spin chemistry.

The methods according to embodiments of the present invention were used to model electron transfer rates between the metalloproteins set forth above and the following substrates: ethylenediaminetetraacetic acid iron (II) (Fe (EDTA)$^{-2}$), tris(1,10-phenanthroline)cobalt(III) (Co (phen)$_3^{+3}$), pentaamminepyridineruthenium(III) (Ru(NH$_3$)$_5$ py$^{+3}$), and tris(oxalato)cobaltate(III) (Co(ox)$_3^{-3}$). Previous studies of the electron transfer between the proteins and these substrates provided data for electron transfer rate, electron transfer potential, protein charges, protein to redox couple distances, protein to active site distances, and substrate self-exchange rates. All of these substrates have a paramagnetic species in either the oxidized or reduced form of the redox couple.

Figure 1:
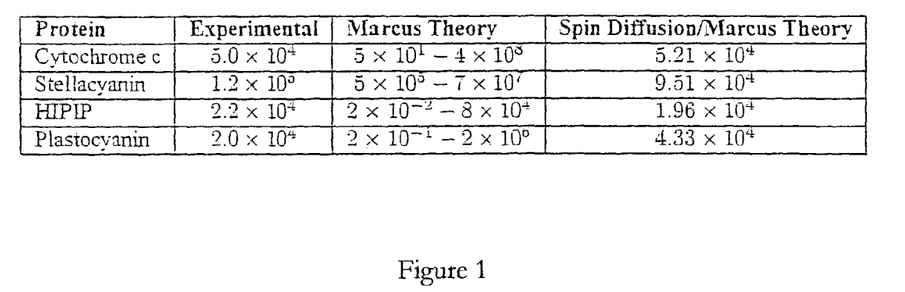
FIG. 1 shows metalloprotein self-exchange rates according to the methods of an embodiment of the present invention (spin diffusion/Marcus theory), conventional Marcus theory and experimentally derived.

The first step in modeling the above protein/substrate electron transfer reactions was to model the protein self-exchange reactions for all four proteins. These protein self-exchange rates have been experimentally determined and they have been modeled using standard Marcus theory methods. FIG. 1 illustrates the range of modeled self-exchange rates using standard Marcus theory methods and the modeled self-exchange rate using the above spin-diffusion/Marcus method, along with the experimental values. The fit of values derived by spin diffusion/Marcus theory model is superior to those derived using the conventional Marcus theory model.

Figure 2:
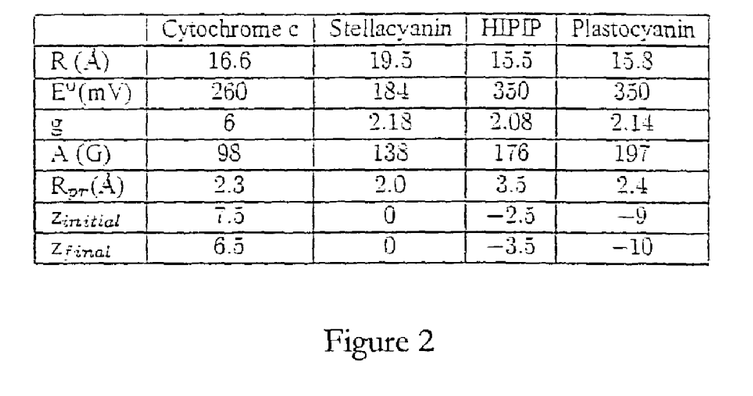
FIG. 2 shows electron transfer metalloprotein data used in practicing methods according to preferred embodiments of the present invention.

The metalloprotein data needed for evaluation of the model are illustrated in FIG. 2. FIG. 2 shows the radius of the protein (R), the formal potential of the protein (E$^\circ$), the electron g-factor (g), the hyperfine coupling constant (A), the distance from metal center to average surface active site ($R_{pr}$), and the initial and final total charges of the proteins ($z_{initial}$ and $z_{final}$). The total charges of the proteins were not used in the calculations, because a small redox couple is not subject to the total protein charge. Approximate calculations were made for the effective charge of the protein in the area of the surface active site. It was found that upon changing these approximations, no significant change in electron transfer rates were observed from the model, because all the systems are spin diffusion limited.

Figure 3:
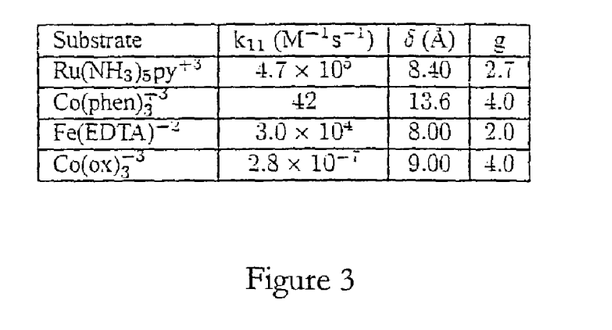
FIG. 3 shows electron transfer substrate data used in practicing methods according to preferred embodiments of the present invention.

The substrate data for the model are illustrated in FIG. 3. FIG. 3 includes the self-exchange rate of the protein ($k_{11}$), the distance of closest approach (or diameter of the substrate molecule, δ), and the g-factor (g).

Figure 4:
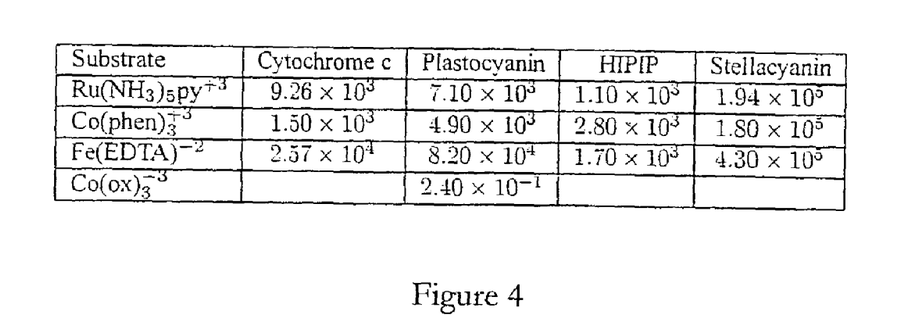
FIG. 4 shows literature values for electron transfer rates between metalloproteins and redox couple substrates.

The overall electron transfer rates between the metalloproteins and substrates were obtained from literature papers. The overall electron transfer rates are illustrated in FIG. 4.

Figure 5:
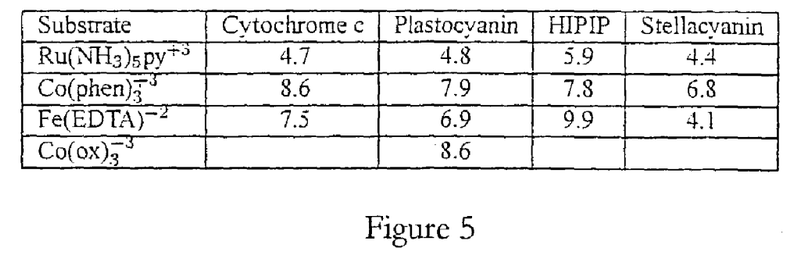
FIG. 5 shows protein metal center to redox couple distances used in practicing methods according to preferred embodiments of the present invention.
Figure 6:
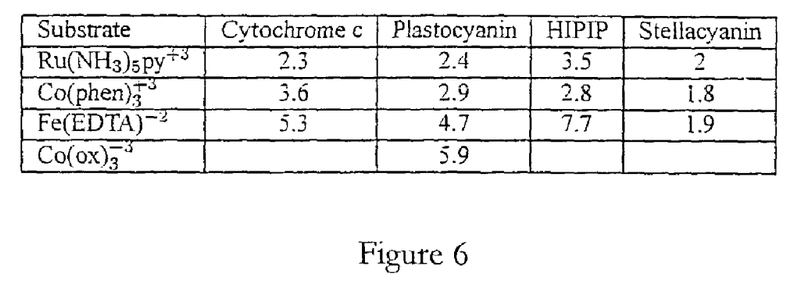
FIG. 6 shows protein metal center to surface active site distances used in practicing methods according to preferred embodiments of the present invention.

The protein metal center to redox couple distance are illustrated in FIG. 5, and the protein metal center to protein surface active site distances are illustrated in FIG. 6. All distances are reported in Angstroms. The protein metal center to redox couple distances (r) provide the distances of closest approach values for the calculating the stability constant in Equation 8. The protein metal center to protein surface active site distances (R) are how far the unpaired electron spin is diffused. The values in FIGS. 2, 3, 4 and 5 were used to calculate stability constants (K), spin polarization rates ($k_{NN}$), spin diffusion rates ($k_{SD}$), and overall electron transfer rates ($k_{ex}$ and $k_{12}$) from Equations 8, 6, 4 and 3, respectively.

Figure 7:
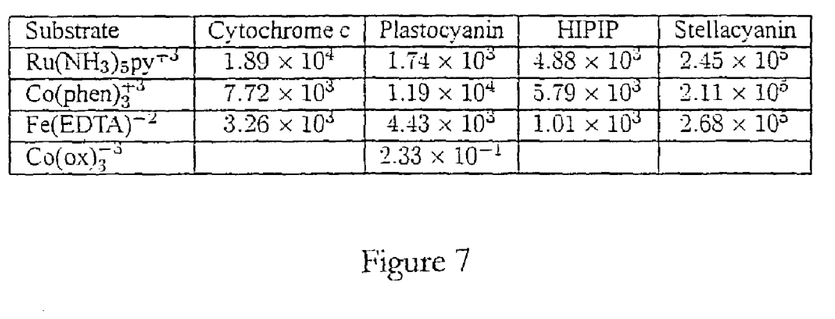
FIG. 7 shows electron transfer rates based on the spin diffusion model according to the present invention.

The electron transfer rates in FIG. 7 were calculated using the literature values above and Equation 9. The corresponding experimental values are illustrated in FIG. 4. The correlation between the modeled electron transfer rates and the literature values is illustrated in FIG. 8.

Figure 8:
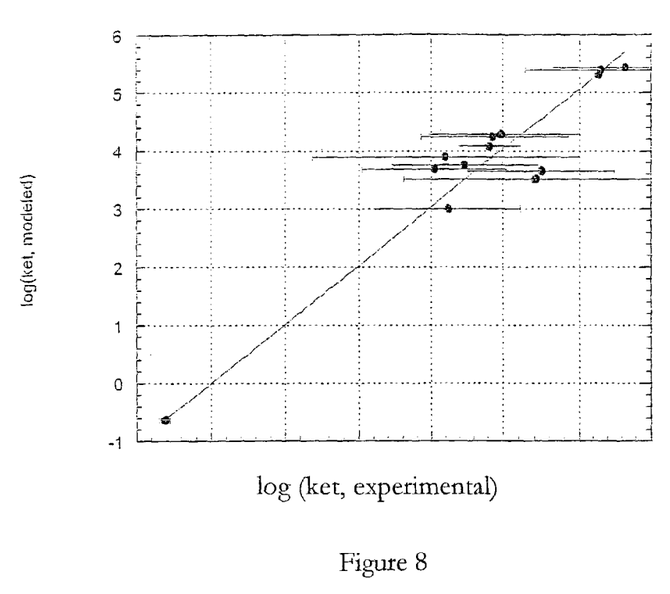
FIG. 8 shows a logarithmic correlation plot for metalloprotein/substrate electron transfer rates determined according to the methods of the present invention.

As can be seen from FIG. 8, the modeled rates agree within the experimental error of the literature values. The weighted regression line for the plot in FIG. 15 is y=(1.00115±0.0142)x+(0.0004±0.0653). The R value is 0.99978. Standard Marcus theory methods are ineffective, because they differ from literature values by ±10$^4$ to ±10$^7$. All of the modeled data developed falls within an order of magnitude of the literature values for the overall electron transfer rates.

Figure 9:
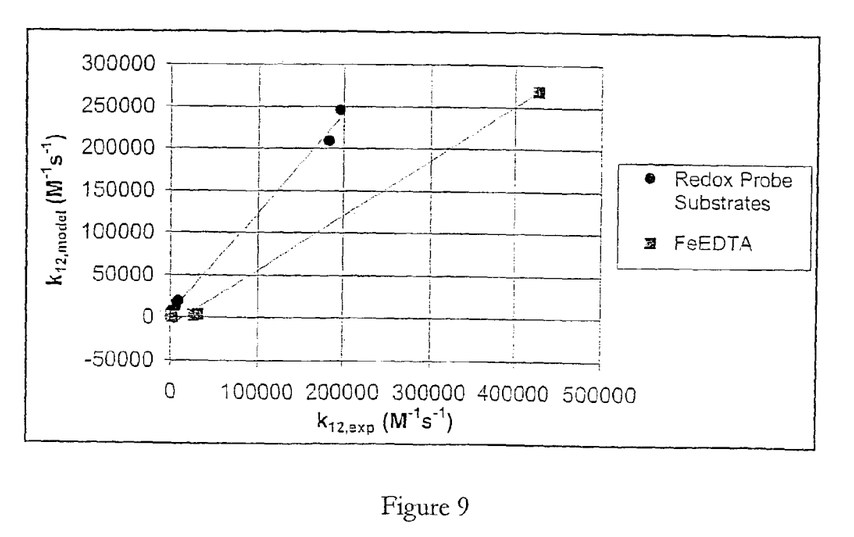
FIG. 9 shows a linear correlation plot for metalloprotein/substrate electron transfer rates determined according to the methods of the present invention.

FIG. 9 is a linear correlation plot for the data shown in FIG. 8. All of the data fall on a single straight line, except for the FeEDTA substrate data. The FeEDTA substrate data fall on a straight line, but lower in slope. The regression line for the redox probe substrates in FIG. 16 is y=(1.1837±0.0276)x+

(4621.5±2459.8). The $R^2$ value is 0.9962. The regression line for the FeEDTA substrate in FIG. 16 is y=(0.6518±0.0239)x+(−9552.6±5125.4). The $R^2$ value is 0.9973.

While not wishing to be bound by theory, it is thought that the FeEDTA substrate data are different from the others because FeEDTA does not undergo a simple outer sphere electron transfer and the equilibria dictate that the experiment solutions contain a trace amount of uncomplexed and partially complexed Fe ions that can undergo a variety of faster electron transfer mechanisms.

The methods according to the present invention can be used to model other systems, such as other protein/substrate electron transfer reactions, protein/protein electron transfer reactions, and protein self-exchange reactions. Examples of other metalloproteins include, but are not limited to, cytochrome oxidase (Fe metal center), ascorbic acid oxidase (Cu metal center), alcohol dehydrogenase (Zn metal center), histidine ammonia-lyase (Mn metal center), glutamate mutase (Co metal center), urease (Ni metal center), xanthine oxidase (Mo metal center), nitrate reductase (V metal center) and glutathione peroxidase (Se metal center).

The spin diffusion/Marcus theory model for electron transfer reactions involving metalloproteins according to the present invention helps to illustrate the importance of metal centers in many biological systems. All of the above protein self-exchange reactions and protein/substrate electron transfer reactions are spin diffusion limited. The electron transfer step from surface active site of the protein to the substrate is fast compared to the spin diffusion, but without spin diffusion there would be no electron-nuclear cross-relaxation facilitated electron transfer. The model allows for cases where the rate of spin diffusion and electron transfer are comparable. Without electron-nuclear cross-relaxation facilitated electron transfer, biological systems would undergo much slower electron transfers because electrons would be required to tunnel through the protein backbone to the substrate over a relatively long distance (10-20 Å). The probability of tunneling through 10 Å of space is small, because tunneling probability decays exponentially.

The methods according to embodiments of the present invention may be used, for instance, in smart drug design and enzyme engineering. The methods according to the present invention make it possible to accurately model how changes in a target molecule will affect electron transfer. For instance, the affects of varying the metal center to surface active site distance on electron transfer rates in metalloprotein systems may be investigated.

The methods according to the present invention may be used to optimize or model devices, such as bioreactors. Similarly, the methods are useful in examining any biological process where electron transfer plays a role.

Regarding smart drug design, the methods according to the present invention, may be used to design drugs that act as substrates and that alter the rate of an enzymatic reaction. For instance, the methods according to the present are useful to model the effects of adding a bridging group between a metal center and active sites of a metalloprotein to alter rates of spin diffusion and, thus electron transfer. Similarly, the effect of replacing the molecular framework of a metalloprotein on rates of spin diffusion and, thus, electron transfer may be modeled according to the methods of the present invention.

Another use of the methods according to the present invention include modeling systems wherein a bridging group connects the metal center of a metalloprotein to a surface active site not known to be involved in a particular reaction. Such structures may allow the protein to shuttle spin and, thus electrons, to generate alternative reaction pathways and rates.

Similarly, the methods according to the present invention may be used to model enzymes or substrates engineered to include a group that does not bridge to a surface active site or substrate. Such systems may short circuit spin diffusion and, thus, electron transfer to the active site or substrate.

The foregoing embodiments and advantages are merely exemplary and are not to be construed as limiting the present invention. The description of the present invention is intended to be illustrative, and not to limit the scope of the claims. Many alternatives, modifications, and variations will be apparent to those skilled in the art.

What is claimed is:

1. A method for determining an electron transfer rate between a metalloprotein and a substrate, which comprises:
   modeling a metalloprotein to determine a distance from a metal center of said metalloprotein to a surface active site of said metalloprotein;
   determining a spin diffusion rate, which corresponds to the rate at which a spin diffuses from said metal center to said surface active site;
   determining an intermediate electron transfer rate value, using a self exchange rate of said metalloprotein, a self exchange rate of said substrate, a stability constant of a complex comprising said metalloprotein and said substrate, and a collision frequency of said metalloprotein and said substrate; and
   modifying said intermediate electron transfer rate value using said spin diffusion rate to yield said electron transfer rate between said metalloprotein and said substrate.

2. The method according to claim 1, wherein said metalloprotein is selected from the group consisting of horse heart cytochrome c, stellacyanin, plastocyanin and HIPIP.

3. The method according to claim 1, wherein said substrate is a metal complex redox couple selected from the group consisting of $Fe(EDTA)^{-2}$, $Co(phen)_3^{-3}$ $Ru(NH_3)_5py^{+3}$ and $Co(ox)_3^{-3}$.

4. The method according to claim 1, wherein said substrate comprises a metal complex redox couple having a paramagnetic species in either the reduced or oxidized form of the redox couple.

5. A method for determining an overall self-exchange rate for a metalloprotein, which comprises:
   modeling said metalloprotein to determine a distance from a metal center of said metalloprotein to a surface active site of said metalloprotein;
   determining a spin diffusion rate, which corresponds to the rate at which a spin diffuses from said metal center to said surface active site;
   determining an approximation of self-exchange rates of said surface active site of said metalloprotein; and
   coupling said spin diffusion rate and said approximation of self-exchange rates of said surface active site to yield said overall self-exchange rate for said metalloprotein.

6. The method according to claim 5, wherein said metalloprotein is selected from the group consisting of horse heart cytochrome c, stellacyanin, plastocyanin and HIPIP.

7. The method according to claim 5, wherein said approximation of self-exchange rates of said surface active site of said metalloprotein is a low magnetic field steady state approximation or a Marcus theory approximation.

8. A method for determining an electron transfer rate between a metalloprotein and a substrate, which comprises:
   determining a magnetically enhanced bimolecular electron transfer rate, $k_{12}$;
   determining a spin diffusion rate, $k_{SD}$;

determining an equilibrium constant to form a reactant complex between said metalloprotein and said substrate, $K_{12}$; and determining said electron transfer rate, k, between said metalloprotein and said substrate according to a relationship: $k=(k_{SD}k_{12})/(k_{SD}+(k_{12}/K_{12}))$.

9. The method according to claim 8, wherein said metalloprotein is selected from the group consisting of horse heart cytochrome c, stellacyanin, plastocyanin and HIPIP.

10. The method according to claim 8, wherein said substrate is a metal complex redox couple selected from the group consisting of $Fe(EDTA)^{-2}$, $Co(phen)_3^{-3}$ $Ru(NH_3)_5 py^{+3}$ and $Co(ox)_3^{-3}$.

11. The method according to claim 8, wherein said substrate comprises a metal complex redox couple having a paramagnetic species in either the reduced or oxidized form of the redox couple.

12. A method for determining an overall self-exchange rate for a metalloprotein, which comprises:

determining a spin diffusion rate, $k_{SD}$;

determining a low magnetic field steady state approximation of self-exchange rates of the surface active sites of said metalloprotein, $k_{NN}(H)$; and determining said overall self-exchange rate for said metalloprotein, $k_{NN}$, according to a relationship: $k_{NN}=(k_{SD}k_{NN}(H))/k_{SD}+k_{NN}(H))$.

13. The method according to claim 12, wherein said metalloprotein is selected from the group consisting of horse heart cytochrome c, stellacyanin, plastocyanin and HIPIP.

\* \* \* \* \*